US008557291B2

(12) United States Patent
Rariy et al.

(10) Patent No.: US 8,557,291 B2
(45) Date of Patent: *Oct. 15, 2013

(54) ABUSE-DETERRENT PHARMACEUTICAL COMPOSITIONS OF OPIOIDS AND OTHER DRUGS

(75) Inventors: Roman V. Rariy, Allston, MA (US); Alison B. Fleming, Attleboro, MA (US); Jane Hirsh, Wellesley, MA (US); Alexander M. Klibanov, Boston, MA (US)

(73) Assignee: Collegium Pharmaceutical, Inc., Canton, MA (US)

( * ) Notice: Subject to any disclaimer, the term of this patent is extended or adjusted under 35 U.S.C. 154(b) by 623 days.

This patent is subject to a terminal disclaimer.

(21) Appl. No.: 12/473,073

(22) Filed: May 27, 2009

(65) Prior Publication Data

US 2009/0297617 A1 Dec. 3, 2009

Related U.S. Application Data

(60) Continuation-in-part of application No. 12/112,993, filed on Apr. 30, 2008, which is a division of application No. 10/614,866, filed on Jul. 7, 2003, now Pat. No. 7,399,488, application No. 12/473,073, which is a continuation-in-part of application No. 12/112,937, filed on Apr. 30, 2008, which is a continuation-in-part of application No. 10/614,866, filed on Jul. 7, 2003, now Pat. No. 7,399,488, application No. 12/473,073, which is a continuation-in-part of application No. 11/149,867, filed on Jun. 10, 2005, now Pat. No. 7,771,707.

(60) Provisional application No. 60/579,191, filed on Jun. 12, 2004, provisional application No. 60/393,876, filed on Jul. 5, 2002, provisional application No. 60/436,523, filed on Dec. 23, 2002, provisional application No. 60/443,226, filed on Jan. 28, 2003, provisional application No. 60/463,514, filed on Apr. 15, 2003, provisional application No. 60/463,518, filed on Apr. 15, 2003.

(51) Int. Cl.
*A61K 9/14* (2006.01)
*A61K 9/20* (2006.01)
*A61K 9/48* (2006.01)

(52) U.S. Cl.
USPC ............ 424/489; 424/464; 424/451; 424/502

(58) Field of Classification Search
None
See application file for complete search history.

(56) References Cited

U.S. PATENT DOCUMENTS

| | | | |
|---|---|---|---|
| 3,015,128 A | 1/1962 | Somerville | |
| 3,336,200 A | 8/1967 | Krause et al. | |
| 3,773,955 A | 11/1973 | Pachter | |
| 3,966,940 A | 6/1976 | Pachter et al. | |
| 3,980,766 A | 9/1976 | Shaw et al. | |
| 4,070,494 A | 1/1978 | Hoffmeister et al. | |
| 4,457,933 A | 7/1984 | Gordon et al. | |
| 4,569,937 A | 2/1986 | Baker et al. | |
| 4,675,140 A | 6/1987 | Sparks et al. | |
| 4,722,941 A | 2/1988 | Eckert et al. | |
| 4,861,598 A | 8/1989 | Oshlak | |
| 4,869,904 A | 9/1989 | Uekama et al. | |
| 5,190,947 A | 3/1993 | Riess et al. | |
| 5,356,467 A | 10/1994 | Oshlack et al. | |
| 5,460,826 A | 10/1995 | Merrill et al. | |
| 5,508,042 A | 4/1996 | Oshlack et al. | |
| 5,756,483 A | 5/1998 | Merkus | |
| 5,849,240 A | 12/1998 | Miller et al. | |
| 5,891,471 A | 4/1999 | Miller et al. | |
| 5,914,129 A * | 6/1999 | Mauskop | 424/464 |
| 5,952,005 A | 9/1999 | Olsson et al. | |
| 5,958,452 A | 9/1999 | Oshlack et al. | |
| 5,958,459 A | 9/1999 | Chasin et al. | |
| 5,965,161 A * | 10/1999 | Oshlack et al. | 424/457 |
| 5,965,163 A | 10/1999 | Miller et al. | |
| 5,968,551 A | 10/1999 | Oshlack et al. | |
| 6,048,736 A | 4/2000 | Kosak | |

(Continued)

FOREIGN PATENT DOCUMENTS

| | | |
|---|---|---|
| EP | 0 253 104 | 1/1988 |
| EP | 0375063 A1 | 6/1990 |

(Continued)

OTHER PUBLICATIONS

Rodriguez et al. (1999) International Journal of Pharmaceutics 183(2): 133-143.

(Continued)

*Primary Examiner* — Lakshmi Channavajjala
(74) *Attorney, Agent, or Firm* — Cooley LLP

(57) ABSTRACT

An abuse-deterrent pharmaceutical composition has been developed to reduce the likelihood of improper administration of drugs, especially drugs such as opioids. In a preferred embodiment, a drug is modified to increase its lipophilicity. In some embodiments the modified drug is homogeneously dispersed within spherical microparticles composed of a material that is either slowly soluble or not soluble in water. In some embodiments the drug containing microparticles or drug particles are coated with one or more coating layers, where at least one coating is water insoluble and/or organic solvent insoluble. The abuse-deterrent composition retards the release of drug, even if the physical integrity of the formulation is compromised (for example, by chopping with a blade or crushing) and the resulting material is placed in water, snorted, or swallowed. However, when administered as directed, the drug is slowly released from the composition as the composition is passes through the GI tract.

19 Claims, No Drawings

(56) References Cited

U.S. PATENT DOCUMENTS

| | | | |
|---|---|---|---|
| 6,068,855 A | 5/2000 | Leslie et al. | |
| 6,103,261 A | 8/2000 | Chasin et al. | |
| 6,156,764 A | 12/2000 | Asmussen et al. | |
| 6,162,467 A | 12/2000 | Miller et al. | |
| 6,255,502 B1 * | 7/2001 | Penkler et al. | 552/549 |
| 6,261,599 B1 | 7/2001 | Oshlack et al. | |
| 6,277,384 B1 | 8/2001 | Kaiko et al. | |
| 6,294,195 B1 | 9/2001 | Oshlack et al. | |
| 6,309,668 B1 | 10/2001 | Bastin et al. | |
| 6,310,072 B1 | 10/2001 | Smith et al. | |
| 6,328,979 B1 | 12/2001 | Yamashita et al. | |
| 6,335,033 B2 | 1/2002 | Oshlack et al. | |
| 6,375,957 B1 | 4/2002 | Kaiko et al. | |
| 6,475,494 B2 | 11/2002 | Kaiko et al. | |
| 6,692,767 B2 | 2/2004 | Burnside et al. | |
| 6,696,088 B2 | 2/2004 | Oshlack et al. | |
| 6,706,281 B2 | 3/2004 | Oshlack et al. | |
| 6,723,343 B2 | 4/2004 | Kugelmann | |
| 6,743,442 B2 | 6/2004 | Oshlack et al. | |
| 6,919,372 B1 | 7/2005 | Yamashita et al. | |
| 7,261,529 B2 | 8/2007 | Persyn et al. | |
| 7,399,488 B2 | 7/2008 | Hirsh et al. | |
| 7,670,612 B2 | 3/2010 | Miller | |
| 7,771,707 B2 * | 8/2010 | Hirsh et al. | 424/10.1 |
| 2002/0032166 A1 | 3/2002 | Shefter et al. | |
| 2002/0081333 A1 | 6/2002 | Oshlack et al. | |
| 2003/0059397 A1 | 3/2003 | Hughes | |
| 2003/0064099 A1 | 4/2003 | Oshlack et al. | |
| 2004/0052731 A1 | 3/2004 | Hirsh et al. | |
| 2004/0062778 A1 | 4/2004 | Shefer et al. | |
| 2005/0013862 A1 | 1/2005 | Tobyn et al. | |
| 2005/0181050 A1 | 8/2005 | Hirsh et al. | |
| 2005/0281748 A1 | 12/2005 | Hirsh et al. | |
| 2006/0104909 A1 | 5/2006 | Vaghefi et al. | |
| 2008/0199530 A1 | 8/2008 | Hirsh et al. | |
| 2008/0260819 A1 | 10/2008 | Fleming et al. | |
| 2010/0260834 A1 | 10/2010 | Hirsh et al. | |
| 2011/0142943 A1 * | 6/2011 | Rariy et al. | 424/489 |

FOREIGN PATENT DOCUMENTS

| | | |
|---|---|---|
| EP | 0578231 A1 | 1/1994 |
| EP | 0 647 448 | 4/1995 |
| GB | 1 513 166 | 6/1978 |
| WO | WO 93/10765 | 6/1993 |
| WO | WO 95/20947 | 8/1995 |
| WO | WO 97/14438 | 4/1997 |
| WO | WO 97/49402 A1 | 12/1997 |
| WO | WO 98/18827 A1 | 5/1998 |
| WO | WO 00/50007 | 8/2000 |
| WO | WO 01/08661 | 2/2001 |
| WO | WO 01/58447 | 8/2001 |
| WO | WO 01/72338 | 10/2001 |
| WO | WO 03/004029 A1 | 1/2003 |
| WO | WO 2004/075877 | 9/2004 |

OTHER PUBLICATIONS

Abuse and Mental Health Services Administration, "Results from the 2004 National Survey on Drug Use and Health: National Findings," pp. 1-310 (2005).

Cortesi, et al., "Sugar cross-linked gelatin for controlled release: microspheres and disks," *Biomaterials* 19: 1641-1649 (1998).

Gennaro, ed., *Remington: The Science and Practice of Pharmacology*, 20$^{th}$ ed., Lipincott: Baltimore, MD, pp. 704-706 (2000).

Nakmura, et al., "Development of an oral sustained release drug delivery system utilizing pH-dependent swelling of carboxyvinyl polymer", *J. Control. Rel.*, 111:309-319 (2006).

"Supplementary European Search Report," 7 pages, EP appl. No. 03763229.6 (Sep. 19, 2008).

"International Preliminary Report on Patentability," 6 pages, PCT appl. No. PCT/US2005/020588 (Oct. 2, 2006).

"International Search Report," 4 pages, PCT appl. No. PCT/US2005/020588 (Sep. 9, 2005).

"Written Opinion of the International Searching Authority," 6 pages, PCT appl. No. PCT/US2005/020588 (Sep. 9, 2005).

"Written Opinion," 4 pages, PCT appl. No. PCT/US03/21095 (Jun. 20, 2004).

"International Search Report," 2 pages, PCT appl. No. PCT/US03/21095 (Nov. 6, 2003).

"International Preliminary Report on Patentability," 3 pages, PCT appl. No. PCT/US03/21095 (Apr. 25, 2005).

"Castor oil, hydrogenated," European Pharmacopoeia V.5, p. 1197-1198 (2005).

Bush et al., "A comparison of a theophylline-ephedrine combination with terbutaline," Ann. Allergy 41:13-17 (1978) abstract.

Chemical Abstract Society (CAS), Properties for HPMC (CAS reg. No. 9004-65-3) accessed Jun. 29, 2013.

Choi et al., "Hydrophobic ion pair formation between leuprolide and sodium oleate for sustained release from biodegradable polymeric microspheres," Int. J. Pharm. 203:193-202 (2000).

Lan et al., "Studies on the Synthesis and Thermal Properties of Copoly(L-lactic acid/glycolic acid) by Direct Melt Polycondensation," J. Appl. Polymer Sci. 92:2163-2168 (2004).

Raffin et al., "Sodium pantoprazole-loaded enteric microparticles prepared by spray drying: Effect of the scale of production and process validation," Int. J. Pharm. 324:10-18 (2006).

Redden et al., "In vitro hydrolysis of polyunsaturated fatty acid N-acyloxymethyl derivatives of theophylline," Int. J. Pharm. 165:87-96 (1998).

\* cited by examiner

ABUSE-DETERRENT PHARMACEUTICAL COMPOSITIONS OF OPIOIDS AND OTHER DRUGS

CROSS REFERENCE TO RELATED APPLICATIONS

This application is a continuation-in-part of U.S. Ser. No. 12/112,993, filed Apr. 30, 2008, which is a divisional of U.S. Ser. No. 10/614,866 filed Jul. 7, 2003, which claims priority to U.S. Ser. No. 60/393,876 filed Jul. 5, 2002 entitled "Abuse-Resistant Formulations of Oxycontin and Other Drugs" by Alexander M. Klibanov, Stephen L. Buchwald, Timothy M. Swager, and Whe-Yong Lo; U.S. Ser. No. 60/436,523 filed Dec. 23, 2002 by Alison B. Fleming, Roman V. Rariy, Alexander M. Klibanov, Whe-Yong Lo, and Jane Hirsh; U.S. Ser. No. 60/443,226 filed Jan. 28, 2003 by Jane Hirsh, Alison B. Fleming, Alexander M. Klibanov, and Whe-Yong Lo; U.S. Ser. No. 60/463,514 filed Apr. 15, 2003 by Jane C. Hirsh, Alison B. Fleming, Roman V. Rariy, Stephen L. Buchwald, and Timothy M. Swager; and U.S. Ser. No. 60/463,518 filed Apr. 15, 2003 by Jane C. Hirsh, Alison B. Fleming and Roman V. Rariy.

This application also is a continuation-in-part of Ser. No. 12/112,937, filed Apr. 30, 2008, which is a continuation-in-part of U.S. Ser. No. 10/614,866, filed Jul. 7, 2003, which claims priority to U.S. Ser. No. 60/393,876 filed Jul. 5, 2002; U.S. Ser. No. 60/436,523 filed Dec. 23, 2002; U.S. Ser. No. 60/443,226 filed Jan. 28, 2003; U.S. Ser. No. 60/463,514 filed Apr. 15, 2003; and U.S. Ser. No. 60/463,518 filed Apr. 15, 2003 and a continuation-in-part of U.S. Ser. No. 11/149,867, filed Jun. 10, 2005, which claims priority to U.S. Ser. No. 60/579,191, filed Jun. 12, 2004.

FIELD OF THE INVENTION

The present invention is generally in the field of pharmaceutical compositions, and specifically compositions that are designed to reduce the potential for improper administration of drugs, such as those subject to abuse.

BACKGROUND OF THE INVENTION

Oxycodone, morphine, and other opioid analgesics are successful and therapeutically useful medications, e.g., as pain killers, when administered orally. Unfortunately, they also pose a severe threat for willful abuse due to their ability to alter mood and/or cause a sense of euphoria. Currently available sustained release formulations of such drugs, which contain a relatively large amount of drug meant to be released from the formulation over an extended time period, are particularly attractive to abusers since the sustained release action can be destroyed by crushing or grinding the formulation. The resulting material (i.e., the crushed formulation) can no longer control the release of drug. Depending on the drug, abusers can then (1) snort the material, (2) swallow the material or (3) dissolve the material in water and subsequently inject it intravenously. The dose of drug contained in the formulation is absorbed immediately through the nasal or GI mucosa (for snorting or swallowing, respectively) or is administered in a bolus to the systemic circulation (for IV injection). These abuse methods result in the rapid bioavailability of relatively high doses of drug, giving the abuser a "high". Since relatively simple methods (crushing, grinding, chewing and/or dissolution in water) can be used to transform such formulations into an abusable form, they provide virtually no deterrent to a potential abuser.

For example, the FDA recently strengthened the warnings and precautions sections in the labeling of OxyContin® (oxycodone HCl controlled-release) tablets, a narcotic drug approved for the treatment of moderate to severe pain, because of continuing reports of abuse and diversion. OxyContin® contains oxycodone HCl (available in 10, 20, 40 and 80 mg strengths), an opioid agonist with an addiction potential similar to that of morphine. Opioid agonists are substances that act by attaching to specific proteins called opioid receptors, which are found in the brain, spinal cord, and gastrointestinal tract. When these drugs attach to certain opioid receptors in the brain and spinal cord they can effectively block the transmission of pain messages to the brain.

OxyContin® is supplied in a controlled-release dosage form and is intended to provide up to 12 hours of relief from moderate to severe pain. The warning specifically states that the tablet must be taken whole and only by mouth. When the tablet is chewed or crushed and its contents are swallowed, snorted into the nostrils or dissolved and subsequently injected intravenously, the controlled release mechanism is destroyed and a potentially lethal dose of oxycodone becomes bioavailable.

In recent years, there have been numerous reports of Oxycodone diversion and abuse in several states. For example, the DEA's Office of Diversion Control reported 700 OxyContin® thefts in the United States between January 2000 and June 2001. Some of these reported cases have been associated with serious consequences including death. According to a report from the Abuse and Mental Health Services Administration, Results from the 2004 National Survey on Drug Use and Health: National Findings (Rockville, Md.: US Dept. of Health and Human Services, Office of Applied Studies, 2005, p. 50), in 2004, the number of new non-medical users of OxyContin® was 615,000, with an average age at first use of 24.5 years. Comparable data on past year Oxycontin® initiation are not available for prior years, but calendar year estimates of Oxycontin® initiation show a steady increase in the number of initiates from 1995, the year this product was first available, through 2003

Oxycodone is a controlled substance in Schedule II of the Controlled Substances Act (CSA), which is administered by the Drug Enforcement Administration (DEA). Despite the fact that Schedule II provides the maximum amount of control possible under the CSA for approved drug products, in practice it is difficult for law enforcement agencies to control the diversion or misuse of legitimate prescriptions. Although abuse, misuse, and diversion are potential problems for all opioids, including Oxycodone, opioids are a very important part of the medical armamentarium for the management of pain when used appropriately under the careful supervision of a physician.

Currently available formulations for such drugs are designed for oral administration but are vulnerable to alterations in their dissolution characteristics by physical manipulation of the formulation as discussed above. Such formulations are also vulnerable due to the inherently high water solubility of the API contained therein. Because of their nature, these formulations do not prevent or deter improper methods of administration such as chewing, injection and snorting. This represents a serious problem given the large number of legitimate prescriptions written in the US; for example, the medical use of opioids within the US increased 400% from 1996 to 2000. The problems with abuse are significant and longstanding, and efforts to design new abuse-resistant or abuse-deterrent formulations have been largely unsuccessful.

U.S. Pat. Nos. 3,980,766 to Shaw et al ("Shaw"), 4,070,494 to Hoffmeister et al. ("Hoffmeister"), and 6,309,668 to Bastin et al. ("Bastin") describe formulations designed to prevent the injection of compositions meant for oral administration.

Shaw describes the incorporation of an ingestible solid which causes a rapid increase in viscosity upon concentration of an aqueous solution thereof.

Hoffmeister describes the incorporation of a non-toxic, water gelable material in an amount sufficient to render the drug resistant to aqueous extraction.

Bastin describes a tablet for oral administration containing two or more layers containing one or more drugs and one or more gelling agents within separate layers of the tablet. The resulting tablet forms a gel when combined with the volume of water necessary to dissolve the drug allegedly reducing the extractability of the drug from the tablet.

It should be noted that although these compositions allegedly preclude abuse by injection, this approach fails to prohibit rapid dissolution of the drug once the dosage form is crushed into smaller particles or pieces. Thus, these formulations are vulnerable to abuse by crushing and swallowing or snorting the formulation, which are commonly reported methods of abuse associated with OxyContin®.

U.S. Pat. Nos. 3,773,955 and 3,966,940 to Pachter et al. describe formulations containing a combination of opioid agonists and antagonists, in which the antagonist does not block the therapeutic effect when the admixture is administered orally, but which does not produce analgesia, euphoria or physical dependence when administered parenterally by an abuser.

U.S. Pat. No. 4,457,933 to Gordon et al. describes a method for decreasing both the oral and parenteral abuse potential of strong analgetic agents by combining an analgesic dose of the analgetic agent with an antagonist in specific, relatively narrow ratios.

U.S. Pat. Nos. 6,277,384, 6,375,957 and 6,475,494 to Kaiko et al describe oral dosage forms including a combination of an orally active opioid agonist and an orally active opioid antagonist in a ratio that, when delivered orally, is analgesically effective but that is aversive in a physically dependent subject. While such a formulation may be successful in deterring abuse, it also has the potential to produce adverse effects in legitimate patients.

It is therefore an object of the present invention to provide a pharmaceutical composition that significantly reduces the potential for improper administration or use of drugs but which, when administered as directed, is capable of delivering a therapeutically effective dose.

SUMMARY OF THE INVENTION

An abuse-deterrent pharmaceutical composition and methods of making and using thereof have been developed. The compositions can be used to reduce the likelihood of improper administration of drugs, especially drugs prone to abuse such as oxycodone. The technology is useful for a number of other drugs where sustained release oral delivery is desired, and there is potential for abuse if the drug dose is made immediately available for nasal, intravenous (IV) or oral administration. In a preferred embodiment, the drug is chemically modified to increase its lipophilicity and is formulated as microparticles. In other embodiments, the formulation contains lipophilic or water-insoluble materials or is made using a process which increases the lipophilicity and/or water-insolubility of the composition. In some embodiments, the composition additionally contains one or more antioxidants.

The abuse-deterrent composition retards the release of drug, even if the physical integrity of the dosage form is compromised (for example, by chopping with a blade or crushing) and the resulting material is placed in water, snorted, or swallowed. However, when administered as directed, the drug is released slowly (typically over a period of 4-18 hours) from the composition by diffusion as the composition is broken down or dissolved gradually within the GI tract by a combination of surfactant action of bile acids, mechanical erosion and/or enzymatic degradation.

In some embodiments, the individual drug-containing microparticles or drug particles are coated with one or more independent coating layers. At least one of the coating materials is water-insoluble and/or organic solvent-insoluble, so that in vitro degradation of the formulation will require more than one step. Thus, the drug is not easily extractable from the formulations by conventional chemical means. In contrast, when administered to the gastrointestinal tract via swallowing, the drug will gradually be released from the coated microparticles as a consequence of diffusion, the gradual break down of the formulation via surfactant action of bile acids, mechanical erosion and/or enzymatic degradation.

The pharmaceutical composition, when administered orally, results in a desired drug release profile. The release profile provides a therapeutic effect for an extended period of time, typically from 6 to 24 hours, preferably from 12 to 24 hours. Additional compositions are provided which achieve a small immediate release dose that precedes the sustained release of drug. The compositions disclosed herein may optionally contain a drug having no appreciable abuse potential.

DETAILED DESCRIPTION OF THE INVENTION

Disclosed herein are an abuse-deterrent pharmaceutical compositions and the method of making and using the compositions.

I. Compositions

As used herein, "composition" refers to the drug dosage unit for administration to a patient. "Composition" may also be used in reference solely to the active ingredient, or to a formulation containing the active ingredient.

The currently available sustained release dosage forms containing narcotic analgesics and other drugs are subject to misuse, in part, because mechanical destruction of the dosage form exposes the encapsulated drug and allows for immediate dissolution of the drug into aqueous media. Three properties of the dosage form that contribute to this outcome are, (1) the high water solubility of the drug salt form; (2) the lack of protection offered by the hydrophilic and/or water soluble excipients in the formulation; and (3) the ease with which the surface area of the formulation is increased by simple chewing or crushing. Susceptibility to simple methods such as chewing or crushing is particularly problematic for monolithic controlled-release dosage forms. For monolithic dosage forms, such as tablets, even splitting the unit into a few pieces (without completely crushing it) can result in a dramatic increase in the dissolution rate.

In the compositions disclosed herein, one or more of these properties are altered in order to achieve an abuse-deterrent composition. Specifically, in the one embodiment, the drug is modified to increase its lipophilicity which reduces its water solubility. The modified drug is then homogeneously dispersed within one or more carrier materials that are either slowly soluble or not soluble in water. Dispersion within these materials further reduces the accessibility of the drug when crushed and exposed to an aqueous media. In some embodiments, the drug may be partially or fully dispersed in the carrier materials on a molecular level. The intimate mixture of modified drug and carrier materials is subsequently formulated into microparticles, producing a formulation whose surface area is minimally influenced by chewing or crushing.

The terms "abuse-deterrent composition" or "abuse-deterrent formulation" are used interchangeably herein to refer to compositions that reduce the potential for improper administration of drugs but that deliver a therapeutically effective dose when administered as directed. Improper administration includes tampering with the dosage form and/or administering the drug by any route other than instructed. For example, for a tablet or capsule, methods of tampering with the dosage form may include, but are not limited to, breaking, crushing, grinding, chewing and/or dissolving the tablet or the contents of the capsule. For oral administration, improper administration includes administering the drug by any route other than via swallowing.

The abuse deterrent compositions preferably contain a drug modified to increase its lipophilicity. In some embodiments, the drug is homogenously dispersed within microparticles composed of a material that is either slowly soluble in water or water insoluble. The compositions maintain the slow the release of drug if the dosage form is chopped or crushed and the resulting material is placed in water, snorted, or swallowed since most of the drug will remain associated with or entrapped within portions of the core material of the microparticles. In other embodiments, the drug containing microparticles or individual drug particles are coated with one or more coating layers, where at least one coating is water insoluble and/or organic solvent insoluble. The components of the resulting coated microparticles are not mutually soluble in water or organic solvents, such that no one solvent or enzyme solution is capable of dissolving the formulation in its entirety in vitro. Therefore, extraction of the drug from the formulation cannot be carried out in one step. However, when administered as directed, the drug is slowly released from the formulation via diffusion and erosion within the environment of the gastrointestinal tract.

A. Drugs to be Formulated

There are many drugs which can be delivered using the compositions described herein. The Controlled Substances Act (CSA), Title II of the Comprehensive Drug Abuse Prevention and Control Act of 1970, places all substances that are regulated under existing federal law into one of five schedules based upon the substance's medicinal value, harmfulness, and potential for abuse or addiction. Drugs that are preferred include those classified as Schedule II, III, IV and V drugs. Drugs that are most preferable include those, like oxycodone, that are currently formulated as sustained or controlled release compositions, where drug release is intended to occur over a prolonged period of time through the gastrointestinal tract, and immediate or burst release, for example, by inhalation or injection, is undesirable. As used herein, drugs prone to abuse refer to controlled substance specified as schedule II, III, IV and V drugs.

The terms "drug", "active agent", and "pharmacologically active agent" are used interchangeably herein to refer to a chemical compound that induces a desired pharmacological, physiological effect. The terms also encompass pharmaceutically acceptable derivatives of those active agents specifically mentioned herein, including, but not limited to, salts, solvates, hydrates, complexes with one or more molecules, prodrugs, active metabolites, analogs, and the like. When the terms "active agent", "pharmacologically active agent" and "drug" are used, or when a particular drug, such as oxycodone, is identified, it is to be understood as including the active agent per se as well as pharmaceutically acceptable salts, solvates, hydrates, complexes with one or more molecules, prodrugs, active metabolites, and analogs.

Examples of preferred drugs include, 1-phenylcyclohexylamine, 1-piperidinocyclohexanecarbonitrile, alfentanil, alphacetylmethadol, alphaprodine, alprazolam, amobarbital, amphetamine, anileridine, apomorphine, aprobarbital, barbital, barbituric acid derivative, bemidone, benzoylecgonine, benzphetamine, betacetylmethadol, betaprodine, bezitramide, bromazepam, buprenorphine, butabarbital, butalbital, butorphanol, camazepam, cathine, chloral, chlordiazepoxide, clobazam, clonazepam, clorazepate, clotiazepam, cloxazolam, cocaine, codeine, chlorphentermine, delorazepam, dexfenfluramine, dextromoramide, dextropropoxyphen, dezocine, diazepam, diethylpropion, difenoxin, dihydrocodeine, dihydromorphine, dioxaphentyl butyrate, dipanone, diphenoxylate, diprenorphine, ecgonine, enadoline, eptazocine, estazolam, ethoheptazine, ethyl loflazepate, ethylmorphine, etorphine, femproponex, fencamfamin, fenfluramine, fentanyl, fludiazepam, flunitrazepam, flurazepam, glutethimide, halazepam, haloxazolam, hexalgon, hydrocodone, hydromorphone, isomethadone, hydrocodone, ketamine, ketazolam, ketobemidone, levanone, levoalphacetylmethadol, levomethadone, levomethadyl acetate, levomethorphan, levorphanol, lofentanil, loperamide, loprazolam, lorazepam, lormetazepam, lysergic acid, lysergic acid amide, mazindol, medazepam, mefenorex, meperidine, meptazinol, metazocine, methadone, methamphetamine, methohexital, methotrimeprazine, methyldihydromorphinone, methylphenidate, methylphenobarbital, metopon, morphine, nabilone, nalbuphine, nalbupine, nalorphine, narceine, nefopam, nicomorphine, nimetazepam, nitrazepam, nordiazepam, normethadone, normorphine, oxazepam, oxazolam, oxycodone, oxymorphone, pentazocine, pentobarbital, phenadoxone, phenazocine, phencyclidine, phendimetrazine, phenmetrazine, pheneridine, piminodine, prodilidine, properidine, propoxyphene, racemethorphan, racemorphan, racemoramide, remifentanil, secobarbital, sufentanil, talbutal, thebaine, thiamylal, thiopental, tramadol, trimeperidine, and vinbarbital.

In addition to the compounds above, the following scheduled drugs may be incorporated into the composition: allobarbitone, alprazolam, amylobarbitone, aprobarbital, barbital, barbitone, benzphetamine, brallobarbital, bromazepam, brotizolam, buspirone, butalbital, butobarbitone, butorphanol, camazepam, captodiame, carbromal, carfentanil, carpipramine, cathine, chloral, chloral betaine, chloral hydrate, chloralose, chlordiazepoxide, chlorhexadol, chlormethiazole edisylate, chlormezanone, cinolazepam, clobazam, potassium clorazepate, clotiazepam, cloxazolam, cyclobarbitone, delorazepam, dexfenfluramine, diazepam, diethylpropion, difebarbamate, difenoxin, enciprazine, estazolam, ethyl loflazepate, etizolam, febarbamate, fencamfamin, fenfluramine, fenproporex, fluanisone, fludiazepam, flunitraam, flunitrazepam, flurazepam, flutoprazepam, gepirone, glutethimide, halazepam, haloxazolam, hexobarbitone, ibomal, ipsapirone, ketazolam, loprazolam mesylate, lorazepam, lormetazepam, mazindol, mebutamate, medazepam, mefenorex, mephobarbital, meprobamate, metaclazepam, methaqualone, methohexital, methylpentynol, methylphenobarbital, midazolam, milazolam, morphine, nimetazepam, nitrazepam, nordazepam, oxazepam, oxazolam, paraldehyde, pemoline, pentabarbitone, pentazocine, pentobarbital, phencyclidine, phenobarbital, phendimetrazine, phenmetrazine, phenprobamate, phentermine, phenyacetone, pinazepam, pipradol, prazepam, proxibarbal, quazepam, quinalbaritone, secobarbital, secbutobarbitone, sibutramine, temazepam, tetrazepam, triazolam, triclofos, zalepan, zaleplon, zolazepam, zolpidem, and zopiclone. Certain compounds described herein may exist in particular geometric or stereoisomeric forms. The composition disclosed herein contemplates all such compounds, including cis- and trans-isomers, R- and S-enantiomers, diastereomers, (D)-isomers, (L)-isomers, the racemic mixtures thereof, compounds of different spacial conformations, and other mixtures thereof, as falling within the scope of the invention. Additional asymmetric carbon atoms may be present in a substituent such as an alkyl group. All such isomers, as well as mixtures thereof, are intended to be included in this invention.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, myristic, palmitic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the compounds can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 20th ed., Lippincott Williams & Wilkins, Baltimore, Md., 2000, p. 704, the disclosure of which is hereby incorporated by reference.

Optionally, the composition described herein can further include a drug having no appreciable abuse potential.

B. Drug Solubility Modification

In some embodiments, the solubility characteristics of a drug are altered. Modification of the drug to produce a more lipophilic derivative serves to reduce the water solubility of the drug and thus reduce the aqueous extractability of the drug. Furthermore, if the drug is made more lipophilic, it can be solubilized in a molten fatty substance or wax like mixture, rather than physically dispersed in a particulate form. Solubilization of the drug enhances the abuse-deterrent properties of microparticles formulated from the mixture as it is difficult to extract drug from an intimately dispersed composition. Furthermore, such a composition is capable of controlling the release of drug, even when formulated into relatively small microparticles. Microparticulate compositions, in contrast to monolithic compositions, are inherently less susceptible to tampering by mechanisms that are intended to increase the surface area and, consequently, the release rate of drug (such as chewing or crushing).

The terms "lipophilic derivative" and "lipophililic drug derivative", as used herein, refer to derivatives of the drug that are less soluble or dissolve less rapidly in water than the most soluble salt of the drug; the most soluble salt being selected from either base addition salts (for acidic drugs) or acid addition salts (for basic drugs), such as by the addition of inorganic acids. The examples of the latter include but are not limited to hydrohalates, sulfates, and nitrates. Some of the methods that can be used to alter the drug's lipophilicity are outlined below. It is understood that two or more approaches can be combined to achieve a desired solubility profile.

Methods for Increasing Lipophilicity

In one embodiment, the drug is made more lipophilic by eliminating or reducing the overall charge of the drug molecule. For example, for a basic drug, a water soluble salt (such as hydrochloride, sulfate, or maleate) can be converted to a free base using techniques known in the art. In the case of an acidic drug, a water soluble salt (such as sodium, potassium, or the like) can be converted to a free acid.

In another embodiment, the drug's lipophilicity is increased by forming a salt between a drug molecule and a charged lipophilic compound. In this case the lipophilicity of the resulting salt can be manipulated by varying the lipophilicity of the counter-ion. In general, lipophilic acids or amines with chain lengths between $C_5$-$C_{30}$ are lipophilic counter-ion candidates. Some specific examples include, but are not limited to, linoleic acid, octanoic acid, lauric acid, stearic acid, palmitic acid, myristic acid, oleic acid, octyl amine, lauryl amine, stearyl amine, palmityl amine, linoleyl amine, and oleyl amine. Other salts which may increase lipophilicity and, hence, lipid solubility relative to the parent drug compound include, but are not limited to, pectinate, tannate, phytate, salicylate, saccharinate, acesulfamate, gallate, and terephthalate salts.

In still a further embodiment, drug lipophilicity is increased via complexation with poorly water-soluble cyclodextrin. For example, ethylated beta-cyclodextrin has been shown to decrease aqueous solubility of complexed drug molecules.

In another embodiment, a drug is covalently modified to increase its lipophilicity. For example, a lipophilic compound can be covalently attached to a drug molecule via an ester or amide linkage. Such drug derivatives are cleaved in vivo, thus releasing the parent compound.

C. Drug Containing Microparticles

In some embodiments, the drug is formulated with a carrier material to form microparticles. As used herein, the term "microparticle" refers to a composition containing a drug dispersed within a carrier material and "coated microparticle" refers to a composition containing a drug containing microparticle or a drug particle coated with one or more coating layers of material. Microparticles and coated microparticles have a size range of 10 to 3000 microns in diameter, more preferably from 10 to 1000 microns.

Within microparticles, the drug is preferably homogeneously dispersed in the form of fine particles within the carrier material. More preferably, the drug is partially solubilized in a molten carrier material or partially dissolved with the carrier material in a mutual solvent during the formulation of the microparticles. Most preferably, the drug is completely solubilized in the molten carrier material or completely dissolved with the carrier material in a co-solvent during the formulation of the microparticles. This is accomplished through the selection of materials and the manner in which they are processed.

Carrier materials appropriate for the fabrication of drug containing microparticles either dissolve slowly in water or are insoluble in water. As used herein, the term "dissolves slowly in water" refers to materials that are not completely dissolved in water within a period of 30 minutes. Suitable materials include fats, fatty substances, waxes, wax-like substances and mixtures thereof. Suitable fats and fatty substances include fatty alcohols (such as lauryl, myristyl stearyl, cetyl or cetostearyl alcohol), fatty acids and derivatives, including but not limited to fatty acid esters, fatty acid glycerides (mono-, di- and tri-glycerides), and hydrogenated fats. Specific examples include, but are not limited to hydrogenated vegetable oil, hydrogenated cottonseed oil, hydrogenated castor oil, hydrogenated oils available under the trade name Sterotex®, stearic acid, cocoa butter, glyceryl behenate (available under the trade name COMPRITOL 888®), glyceryl dipalmitostearate (available under the trade name PRECIROL®), and stearyl alcohol. Mixtures of mono-, di- and tri-glycerides and mono- and di-fatty acid esters of polyethylene glycol, available under the trade name GELUCIRE®) are also suitable fatty materials. Suitable waxes and wax-like materials include natural or synthetic waxes, hydrocarbons, and normal waxes. Specific examples of waxes include beeswax, glycowax, castor wax, carnauba wax, paraffins and candelilla wax. As used herein, a wax-like material is defined as any material which is normally solid at room temperature and has a melting point of from about 30 to 300° C.

In some cases, it may be desirable to alter the rate of water penetration into the hydrophobic drug containing microparticles. To this end, rate-controlling (wicking) agents may be formulated along with the fats or waxes listed above. Examples of rate-controlling materials include certain starch derivatives (e.g., waxy maltodextrin and drum dried corn starch), cellulose derivatives (e.g., hydroxypropylmethylcellulose, hydroxypropylcellulose, methylcellulose, and carboxymethylcellulose), alginic acid, lactose and talc. Additionally, a pharmaceutically acceptable surfactant (for example, lecithin) may be added to facilitate the degradation and/or dissolution of the microparticles.

Proteins which are water insoluble, such as zein, are suitable carrier materials for the formation of drug containing microparticles. Additionally, proteins, polysaccharides and combinations thereof which are water soluble can be formulated with drug into microparticles and subsequently cross-linked to form an insoluble network. For example, cyclodextrins can be complexed with individual drug molecules and subsequently cross-linked.

Certain polymers may also be used as carrier materials in the formulation of drug containing microparticles. Suitable polymers include ethylcellulose and other natural or synthetic cellulose derivatives. Polymers which are slowly soluble and form a gel in an aqueous environment, such as hydroxypropyl methylcellulose or polyethylene oxide may also be suitable as carrier materials for drug containing microparticles.

Encapsulation or incorporation of drug into carrier materials to produce drug containing microparticles can be achieved through known pharmaceutical formulation techniques. To create a composition that protects drug from exposure upon mechanical disruption (eg, grinding, chewing, or chopping), the drug is intimately dispersed within the carrier material. In the case of formulation in fats, waxes or wax-like materials, the carrier material is heated above its melting temperature and the drug is added to form a mixture containing drug particles suspended in the carrier material, drug dissolved in the carrier material, or a mixture thereof. Microparticles can be subsequently formulated through several methods including, but not limited to, congealing, extrusion, spray chilling or aqueous dispersion. In a preferred process, one or more carrier materials are heated above its melting temperature, the drug is added, and the molten carrier material-drug mixture is congealed to form solid, spherical particles via a spraying or spinning cylinder or disk processes.

Alternatively, the molten carrier material-drug mixture can be extruded and pelletized to form pellets or beads. Detailed descriptions of these processes can be found in "Remington—The science and practice of pharmacy", 20$^{th}$ Edition, Jennaro et. Al., (Phila, Lippencott, Williams, and Wilkens, 2000. Spinning disk processes are described in U.S. Pat. Nos. 3,015,128 and 7,261,529.

In a preferred process, spherical particles are produced. Spherical particles may introduce an additional barrier to deter tampering with the composition. Smaller, round particles act as "ball bearings" that are more difficult to crush or grind, and if crushed, do not allow for significant decrease in particle size or surface areas of the particles in order to effect an increase in release rate.

For compositions containing salts composed of a pharmaceutically active agent and one or more fatty acids or amines, the salt may be formed during the formulation process itself. To accomplish this, the one or more fatty acids or amines are melted and mixed with the free base or acid form of the active agent at a temperature above the melting point(s) of the fatty acids) or amine(s). Once a homogeneous mixture is formed, one or more additional carrier materials, such as fat, fatty substance(s), wax or wax-like substance(s) can be added to the molten mixture to yield a single phase composition. The molten solution is then solidified into microparticles using one of the techniques described above.

The molar concentration of fatty acid or amine may need to be higher than that of the drug in order to achieve a homogeneous single phase. For example, it has been found that, for oxycodone, a molar ratio in excess of about 7:1 (fatty acid to drug) results in a homogeneous melt using this technique. The molar ratio needed to obtain a homogeneous melt may depend on the type and quantity of additional carrier materials added. In one embodiment, the molar ratio of fatty acid or fatty amine is from about 1:1 to about 15:1, preferably from about 6:1 to about 15:1. However, molar ratios greater than 15:1, for example 15:1 to 25:1, preferably 15:1-20:1, may be required depending on the fatty acid or fatty amine, the drug to be formulated, and/or the carrier material(s).

For some carrier materials it may be desirable to use a solvent evaporation technique to produce drug containing microparticles. In this case drug and carrier material are co-dissolved in a mutual solvent and microparticles can subsequently be produced by several techniques including, but not limited to, forming an emulsion in water or other appropriate media, spray drying or by evaporating off the solvent from the bulk solution and milling the resulting material.

In addition to modification of the drug itself, processing conditions can be used to influence the dispersion of the drug within water-insoluble or slowly water soluble materials. For example, in the case where the water in-soluble or slowly soluble material is melted and the drug is fully or partially dissolved under stirring conditions, the temperature, agitation rate and time of processing will influence the degree of dissolution achieved. More specifically, a more homogenous dispersion may be achieved with a higher temperature, faster stirring rate and/or longer processing time. Ultrasound can also be applied to the molten mixture to increase the degree of dispersion and/or the rate of dissolution of the drug.

In some embodiments, the drug in a particulate form is homogeneously dispersed in a water-insoluble or slowly water soluble material. To minimize the size of the drug particles within the composition, the drug powder itself may be milled to generate fine particles prior to formulation. The process of jet milling, known in the pharmaceutical art, can be used for this purpose. In some embodiments drug in a particulate form is homogeneously dispersed in a wax or wax like substance by heating the wax or wax like substance above its melting point and adding the drug particles while stirring the mixture. In this case a pharmaceutically acceptable surfactant may be added to the mixture to facilitate the dispersion of the drug particles.

D. Coated Drug Containing Microparticles

In some embodiments, drug containing microparticles or drug particles are encapsulated. Drug containing microparticles can be encapsulated in water insoluble materials, slowly water soluble materials, organic insoluble materials and/or materials with pH dependent solubilities.

In general, any coating procedure which provides a contiguous coating on each microparticle can be used. Coating procedures known in the pharmaceutical arts include, but are not limited to, fluid bed coating processes and microencapsulation may be used to obtain appropriate coatings. Detailed descriptions of these processes can be found in "Remington—The science and practice of pharmacy", $20^{th}$ Edition, Jennaro et. Al., (Phila, Lippencott, Williams, and Wilkens, 2000.

The water-insoluble coating materials may be selected from natural or synthetic film-formers used singly, in admixture with each other, and in admixture with plasticizers, pigments and other substances to alter the characteristics of the coating. A water-insoluble but water-permeable diffusion barrier may contain ethyl cellulose, methyl cellulose and mixtures thereof. The water-permeable diffusion barrier may also include ammonio methacrylate copolymers sold under the trade name EUDRAGIT® (Rohm Pharma), such as EUDRAGIT RS, EUDRAGIT RL, EUDRAGIT NE and mixtures thereof. Other synthetic polymers, for example, polyvinyl acetate (available under the trade name KOLLICOAT®), can also be used to form water-insoluble but permeable coatings.

The coating may also include a water-insoluble but enzymatically degradable material. In some instances the substrates of digestive enzymes are naturally water-insoluble and can be utilized in the formulation without further processing. Solid esters of fatty acids, which are hydrolyzed by lipases, can be spray coated onto microparticles or drug particles. Mixtures of waxes (beeswax, carnauba wax, etc.) with glyceryl monostearate, stearic acid, palmitic acid, glyceryl monopalmitate and cetyl alcohol will also form films that are dissolved slowly or broken down in the GI tract. Zein is an example of a naturally water-insoluble protein. It can be coated onto drug containing microparticles or drug particles by spray coating or by wet granulation techniques. In addition to naturally water-insoluble materials, some substrates of digestive enzymes can be treated with cross-linking procedures, resulting in the formation of non-soluble networks. Many methods of cross-linking proteins, initiated by both chemical and physical means, have been reported. In some embodiments, chemical cross-linking agents are used. Examples of chemical cross-linking agents include aldehydes (gluteraldehyde and formaldehyde), epoxy compounds, carbodiimides, and genipin. In addition to these cross-linking agents, oxidized and native sugars have been used to cross-link gelatin (Cortesi, R., et al., Biomaterials 19 (1998) 1641-1649). Cross-linking can also be accomplished using enzymatic means; for example, transglutaminase has been approved as a GRAS substance for cross-linking seafood products. Finally, cross-linking can be initiated by physical means such as thermal treatment, UV irradiation and gamma irradiation.

To produce a coating layer of cross-linked protein surrounding drug containing microparticles or drug particles, a water soluble protein can be spray coated onto the microparticles and subsequently cross-linked by one of the methods described above. Alternatively, drug containing microparticles can be microencapsulated within protein by coacervation-phase separation (for example, by the addition of salts) and subsequently cross-linked. Some suitable proteins for this purpose include gelatin, albumin, casein, and gluten.

Polysaccharides can also be cross-linked to form a water-insoluble network. For many polysaccharides, this can be accomplished by reaction with calcium salts or multivalent cations which cross-link the main polymer chains. Pectin, alginate, dextran, amylose and guar gum are subject to cross-linking in the presence of multivalent cations. Complexes between oppositely charged polysaccharides can also be formed; pectin and chitosan, for example, can be complexed via electrostatic interactions. Insoluble coatings can be formed on particles in this fashion. It should be noted that in many cases polysaccharides are broken down specifically by enzymes produced by bacteria within the colon.

In some cases a water-insoluble but enzymatically degradable coating including both a protein and a polysaccharide can be produced if the components are oppositely charged polyelectrolytes. Under the proper temperature, pH, and concentrations, the two polymers can interact through their opposite electrical charges and form a water-insoluble complex. If a core particle is present at the time the complex phase separates, it will be coated. For example, gelatin and gum arabic can be coated onto a core particle utilizing this process. Optionally, the complex can be made irreversibly insoluble by subsequent cross-linking induced by chemical or physical means.

Coating materials may also include a pH sensitive polymer which is insoluble in the acid environment of the stomach, and soluble in the more basic environment of the GI tract. These coatings, referred to as enteric coatings, create a dosage form designed to prevent drug release in the stomach. Preventing drug release in the stomach has the advantage of reducing side effects associated with irritation of the gastric mucosa and/or of minimizing exposure of drug to very low pH. Avoiding release within the stomach can be achieved using enteric coatings known in the art. The enteric coated formulation remains intact or substantially intact in the stomach, however, once the formulation reaches the small intestines, the enteric coating dissolves and exposes either drug-containing carrier particles or drug-containing carrier particles coated with extended release coating.

Enteric coated particles can be prepared as described in "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et. al., (Media, Pa.: Williams and Wilkins, 1995). Examples of suitable coating materials include, but are not limited to, cellulose polymers, such as cellulose acetate phthalate, hydroxypropyl cellulose, hydroxypropyl methylcellulose phthalate and hydroxypropyl methylcellulose acetate succinate; polyvinyl acetate phthalate, acrylic acid polymers and copolymers, and certain methacrylic resins that are commercially available under the trade name EUDRAGIT® (Rohm Pharma). Additionally the coating material may contain conventional carriers such as plasticizers, pigments, colorants, glidants, stabilization agents, and surfactants.

In some cases it may be desirable to coat the particles with a coating which is soluble in aqueous solutions but insoluble in hydroalcoholic solutions. In this case the coating material may or may not have pH sensitive solubility in aqueous solutions.

In other cases it may be desirable to combine coating materials to produce a tailored release of drug. For example, combinations of insoluble polymers and pH dependent polymers can produce a pH dependent sustained release profile. Combinations of insoluble polymers (eg, ethylcellulose), water-soluble polymers (eg, HPMC or PEG) and pH dependent swellable polymers (eg, carboxyvinylpolymer) have also been reported to produce pH dependent sustained release profiles (See, for example, Journal of Controlled Release, 2006, 111:309-315).

In one embodiment, the particles are coated with cellulose acetate phthalate. Cellulose acetate phthalate is typically used as an enteric coating.

E. Antioxidants

In some embodiments, the composition includes one or more anti-oxidants. Suitable antioxidants include, but are not limited to, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

Antioxidants may be necessary to prevent oxidative degradation of the active pharmaceutical ingredient and/or the one or more inactive carrier materials in the composition. Oxidation of one or more components may occur during the formulation process itself or during the shelf-life of the composition. Oxidation may result from exposure to the oxygen content of air or, alternatively, may be related to impurities in the carrier materials. For example, highly reactive species such as peroxides, superoxides, hypochlorites and formic acid may be present in carrier materials as manufacturing-related impurities. Also, trace metal impurities in carrier materials, such as iron and copper, can catalyze oxidation reactions. An antioxidant may be included in the composition to mitigate the degradation of the drug in such cases. If the source of oxidation is a reactive manufacturing-related impurity in one or more of the carrier materials, the anti-oxidant can be co-melted with the carrier materials prior to the introduction of the drug into the formulation in order to protect the drug from these reactive species.

The concentration of the antioxidant is generally from about 0.001% to about 1% w/w, preferably from about 0.01% to about 0.5% w/w. However, concentrations of less than 0.001% or greater than 0.5% may be used, provided the concentration is sufficient to stabilize the formulation and is non-toxic.

F. Dosage Forms

In one embodiment a drug is partially dissolved within a water-insoluble or slowly water soluble material during the manufacturing process, for example, by mixing at a temperature above the melting point of the carrier material, and the mixture is formulated into microparticles. In another embodiment a drug is fully dissolved within a water-insoluble or slowly water soluble material during the manufacturing process, for example, by mixing at a temperature above the melting point of the carrier material, and the mixture is formulated into microparticles. In still a further embodiment, the drug containing microparticles, where the drug is homogeneously dispersed in a particulate form, or has been partially or fully dissolved within the carrier material during the manufacturing process, are coated with one or more coatings to form coated microparticles. In a further embodiment, drug particles are coated directly with one or more coatings to form coated microparticles.

The microparticles, coated microparticles, or a mixture thereof are formed into a solid dosage form suitable for oral administration. For example, microparticles or coated microparticles can be incorporated into hard shell capsules, dispersed within a soft gelatin capsule, or combined with appropriate excipients such as magnesium stearate as lubricant, colloidal silicon dioxide as glidant, sodium starch glycolide, sodium croscarmellose or crospovidone as disintegrant, sodium dodecyl sulfate or Polyoxyethylene (20) sorbitan monooleate, polyvinyl pyrrolidone or hydroxypropylmethylcellulose as crystallization inhibitor, and lactose and microcrystalline cellulose as fillers, and tableted by compression.

In some embodiments, the compositions are coated with an enteric coating. Enteric coatings known in the art are applied directly to the abuse-deterrent microparticle or coated microparticle compositions or are applied to the surface of a capsule or tablet containing the abuse deterrent microparticle and/or coated microparticle compositions. Enteric coatings known in the art include, for example, acrylic polymers that are commercially available under the trade name EUDRAGIT®, cellulose acetate phthalate, hydroxypropylmethyl-cellulose phthalate, polyvinylacetate phthalate, shellac, hydroxypropylmethylcellulose succinate, cellulose acetate trimelliate or mixtures thereof. In one embodiment, the particles are coated with cellulose acetate phthalate.

Dosage forms can include one or more drags. When the dosage form includes two or more drugs they can be Scheduled drugs or can be a combination of Scheduled and non-Scheduled drugs. The drugs can be incorporated into separate microparticle compositions where the Scheduled drugs are incorporated into abuse deterrent microparticle compositions and the non-Scheduled drugs are incorporated into abuse deterrent microparticle compositions, sustained release compositions known in the art or immediate release compositions known in the art. The compositions containing the different drugs are formulated into a single solid dosage form suitable for oral administration, for example, they can be incorporated into a gelatin capsule, or combined with appropriate excipients and compressed into a tablet form. Examples of non-scheduled drugs that may be included in dosage forms described herein include, but are not limited to, aspirin, acetaminophen, non-steroidal anti-inflammatory drugs, cyclooxygenase II inhibitors, N-methyl-D-aspartate receptor antagonists, glycine receptor antagonists, triptans, dextromethorphan, promethazine, fiorinal, guaifenesin, butalbital, and caffeine.

An immediate release dose can be incorporated into the formulation in several ways. Immediate release microparticles can be made utilizing standard methodologies and formulated along with abuse-deterrent microparticle and/or coated microparticle compositions in a suitable oral dosage form. Alternatively, a coating containing drug which is available for immediate release can be placed on a tablet containing abuse-deterrent microparticle and/or coated microparticle compositions plus appropriate excipients. Additionally, an immediate dose of drug can be granulated or blended with rapidly dissolving excipients and subsequently compressed (1) as one layer of bi-layer tablets in which the abuse-deterrent microparticle and/or coated microparticle compositions are compressed as the other layer, or (2) as the outer layer of compression-coated tablets in which the abuse-deterrent microparticle and/or coated microparticle compositions are compressed as the inner core, or (3) into tablets in which abuse-deterrent microparticle and/or coated microparticle compositions are embedded.

In some embodiments, the immediate release portion of the dosage form contains a lipophilic drug derivative. For example, salt derivatives or complexes that are insoluble at a neutral pH but dissociate, thereby releasing the parent compound, at an acidic pH are ideal for immediate release within the stomach. In the case of oxycodone some salts that may exhibit this property include, but are not limited to, the tannate, phthalate, salicylate, gallate, pectinate, phytate, saccharinate, asesulfamate and terephthalate salts. Complexes of drug with one or more metal ions and, optionally, one or more lipophilic counter-ions may also be used for immediate drug release. Use of salts or complexes in the immediate release portion of the dosage form reduces the abuse potential of the immediate release dose if the formulation is crushed and (1) snorted or (2) dissolved in water since these salts will be poorly soluble under these conditions. It is understood by the one of ordinary skill in the art that such salts or complexes may also be used to formulate an immediate release dosage form without a sustained release portion.

Additional mechanisms to reduce the potential for abuse can also be incorporated during the process of formulating tablets. For example, ingredients can be added to deter chewing or snorting of the final formulation. For example, an intensely bitter substance may deter chewing, while an intensely spicy ingredient, such as capsaicin, may deter snorting. The addition of a colored dye, which would stain the skin and mucosal surface of the nose following snorting may also serve to reduce this practice.

Optional excipients present in the oral dosage form containing abuse deterrent microparticles or coated microparticles include, but are not limited to diluents, binders, lubricants, disintegrants, colorants, plasticizers and the like. Diluents, also termed "fillers," are typically necessary to increase the bulk of a solid dosage form so that a practical size is provided for compression of tablets. Examples of diluents include cellulose, dry starch, microcrystalline cellulose, dicalcium phosphate, calcium sulfate, sodium chloride confectioner's sugar, compressible sugar, dextrates, dextrin, dextrose, sucrose, mannitol, powdered cellulose, sorbitol, and lactose. Binders are used to impart cohesive qualities powdered materials and can include materials such as starch, gelatin, sugars, natural and synthetic gums, polyethylene glycol, ethylcellulose, methylcellulose, hydroxypropylmethylcellulose, carboxymethylcellulose, waxes and polyvinyl pyrrolidone. Lubricants are used to facilitate tablet manufacture; examples of lubricants include talc, magnesium stearate, calcium stearate, hydrogenated vegetable oils stearic acid, sodium stearyl fumarate, sodium benzoate, sodium acetate, leucine, sodium oleate, sodium lauryl sulfate, magnesium lauryl sulfate and polyethylene glycol. Disintegrants can be added to pharmaceutical formulations in order to facilitate "breakup" or disintegration after administration. Materials used for this purpose include starches, clays, celluloses, aligns, gums, and cross-linked polymers. A plasticizer may be included in coating materials to alter their mechanical properties. Examples of plasticizers include benzyl benzoate, chlorobutanol, dibutyl sebacate, diethyl phthalate, glycerin, mineral oil, polyethylene glycol, sorbitol, triacetin, triethyl citrate, glycerol, etc. In addition to the additives above, coloring and flavoring agents may also be incorporated into the composition.

II. Methods of Administration

In addition to providing a deterrent to common methods of abuse/diversion, the formulation can provide a sustained release of drug over an extended time period. This is a natural consequence of the fact that, in the present formulation, drug is slowly released from a predominantly water-insoluble, hydrophobic matrix as it passes through the GI tract. The barrier components may be degraded as the matrix passes through the GI tract, for example, by enzymes, the surfactant action of bile acids and mechanical erosion.

In some embodiments, an immediate release of drug is achieved within the stomach in order to provide rapid therapeutic onset.

The pharmaceutical drug composition is administered orally. The appropriate dosage formulations can be obtained by calculation of the pharmacokinetics of the formulation, then adjusting using routine techniques to yield the appropriate drug levels based on the approved dosage forms. Any suitable amount of drug containing microparticles or coated microparticles can be included in the final formulation. The selection of a suitable amount of drug containing microparticles depends on the dosage desired and is readily determined by those skilled in the art.

In addition to oral administration, some embodiments may also be administered by other routes, including, but not limited to, rectal and nasal administration. Some embodiments may also be suitable for formulation as oral liquids.

The present composition and method of making and using the composition will be further understood by reference to the following non-limiting examples.

EXAMPLES

Example 1

Preparation of Drug Containing Microparticles

TABLE 1

| | Compositions | | | |
|---|---|---|---|---|
| Ingredient | Composition of Formulation A | Composition of Formulation B | Composition of Formulation C | Composition of Formulation D |
| Oxycodone Base | 5 g | 5 g | 10 g | 5 g |
| Myristic Acid | — | — | 50 g | 30 g |
| Stearic Acid | 34 g | 34 g | — | — |
| Yellow Beeswax | 10 g | — | 10 g | 10 g |
| Carnauba wax | 5 g | 10 g | 20 g | 10 g |

Procedure:

1. Fatty acid (myristic or stearic acid) was melted in an erlenmeyer flask in a silicone oil bath at 100° C. The mixture was stirred and kept under an argon blanket for this and all subsequent steps.

2. Oxycodone base was introduced into the molten fatty acid and the melt was stirred until the oxycodone base was completely dissolved and a clear liquid was formed.

3. Yellow beeswax was added and dissolved under constant stirring.

4. Carnauba wax was added and dissolved under constant stirring.

5. The resulting homogeneous molten solution was poured onto aluminum foil and allowed to solidify at room temperature.

6. The bulk material obtained was combined with small quantities of dry ice and subjected to size reduction in a mortar and pestle.

7. The dry ice was allowed to dissipate and the particles were sieved to obtain various size ranges. Particles 20-40 mesh in size (400-841 micron) were subjected to testing.

Example 2

Release of Drug from Crushed Microparticles

In vitro testing was conducted in order to assess the influence of crushing of the microparticles produced in Example 1 on the release in simulated stomach conditions. A currently marketed sustained release formulation of oxycodone, Oxy-Contin®, was also subjected to crushing and dissolution for comparison purposes.

Microparticles (Formulations A, B, C or D, all 20-40 mesh in starting particle size) or tablets were crushed using a glass mortar & pestle. The resulting crushed material was placed in a dissolution vessel equipped with paddles (USP Apparatus II). 900 mL of 0.1N HCl pre-warmed to 37° C. was added to the vessels and stirred for 15 minutes. After 15 minutes the amount of oxycodone released was determined. The results are shown in Table 2.

TABLE 2

Drug Release from Crushed Compositions

| Sample | % Released in 15 minutes in 0.1N HCl (n = 3) |
|---|---|
| Oxycontin ® (40 mg Tablet) | 95.6 +/− 2.1 |
| Formulation A (microparticles containing 40 mg oxycodone HCl equivalent) | 31.6 +/− 2.6 |
| Formulation B (microparticles containing 40 mg oxycodone HCl equivalent) | 19.7 +/− 1.4 |
| Formulation C (microparticles containing 20 mg oxycodone HCl equivalent) | 14.8 +/− 1.1 |
| Formulation D (microparticles containing 20 mg oxycodone HCl equivalent) | 18.2 +/− 1.6 |

As illustrated in the table above, the microparticle compositions of Example 1 release only a fraction of the total drug load in simulated stomach conditions when crushed. In contrast, a currently marketed sustained release composition, OxyContin®, releases approximately 96% of the drug load when crushed and exposed to identical conditions.

Example 3

Preparation of Oxycodone Containing Microparticles Using a Spinning Disk Atomization Process Batch size: 1000 g

| Component | Quantity(g)/Batch |
|---|---|
| Oxycodone base | 91 |
| Myristic acid | 545 |
| Beeswax | 182 |
| Carnauba Wax | 182 |
| Total | 1000.0 |

Procedure:
1. Myristic acid was melted at 85° C. in a silicone oil bath while constantly flowing argon above the surface of the solution.
2. Beeswax was added to the molten fatty acid and mixed until a clear, homogeneous solution was obtained.
3. Carnauba wax was added to the molten solution and mixed until a clear, homogeneous solution was obtained.
4. Oxycodone base was added to the molten solution and mixed until a clear, homogeneous solution was obtained.
5. The resulting molten solution was transferred to a feed kettle and continuously metered onto a spinning disk atomizer in order to form solid, spherical microparticles.

Example 4

Preparation of Coated Drug Containing Microparticles

The drug-containing particles from Example 3 can be spray coated with cellulose acetate phthalate

Example 5

Preparation of Oxymorphone Containing Microparticles

Batch size: 630.6 g

| Component | Quantity(g)/Batch |
|---|---|
| Oxymorphone base | 60 |
| Stearic Acid | 420 |
| Beeswax | 30 |
| Carnauba Wax NF | 120 |
| Butylated Hydroxyanisole | 0.6 |
| Total | 630.6 |

Procedure:
1. Stearic acid was melted in an erlenmeyer flask in a silicone oil bath at 100° C. Note the composition was subjected to stirring and was kept under an argon blanket for this and all subsequent steps.
2. Butylated hydroxyanisole was added to the molten stearic acid while mixing.
3. Oxymorphone base was introduced into the molten fatty acid and the melt was stirred until all oxymorphone base dissolved and a clear liquid was formed.
4. Beeswax was added and dissolved under constant stirring.
5. Carnauba wax was added and dissolved under constant stirring.
6. The resulting homogeneous molten solution was poured onto aluminum foil and allowed to solidify at room temperature.
7. The bulk wax obtained was combined with dry ice and subjected to size reduction in a mortar and pestle.
8. The dry ice was allowed to dissipate and the particles were sieved to obtain particles in the 40-80 mesh size range.

Example 6

Preparation of Capsules for Oral Administration

The drug containing microparticles from Examples 1, 3, 4, or 5 can be blended with a lubricant and incorporated into standard hard gelatin capsules

We claim:
1. An abuse-deterrent oral dosage form comprising a plurality of microparticles, where each microparticle comprises:

a fatty acid salt of one or more drugs prone to abuse; and
one or more carrier material(s) comprising fats, fatty substances, waxes, wax-like substances or mixtures thereof wherein the oral dosage form retards the release of the one or more drugs prone to abuse, even if the physical integrity of the dosage form is compromised and the compromised dosage form is placed in water.

2. An abuse-deterrent oral dosage form comprising a plurality of microparticles, where each microparticle comprises:
a solidified solution of a fatty acid salt of one or more drugs prone to abuse; and
one or more carrier material(s) comprising fats, fatty substances, waxes, wax-like substances or mixtures thereof.

3. The abuse-deterrent oral dosage form according to claim 2, wherein the oral dosage form retards the release of the one or more drugs prone to abuse, even if the physical integrity of the dosage form is compromised and the compromised dosage form is placed in water.

4. The abuse-deterrent oral dosage form according to claim 1 or 2, wherein the one or more drugs prone to abuse is an opioid.

5. The abuse-deterrent oral dosage form of claim 4, wherein the opioid is an opioid agonist.

6. The abuse-deterrent oral dosage form of claim 5, wherein the opioid agonist is hydrocodone, hydromorphone, morphine, oxycodone, oxymorphone or tramadol.

7. The abuse-deterrent oral dosage form according to claim 1 or 2, wherein the fatty acid salt is the stearate, palmitate or the myristate fatty acid salt.

8. The abuse-deterrent oral dosage form according to claim 1 or 2, wherein the one or more carrier materials comprise myristic acid, stearic acid, palmitic acid, beeswax, carnauba wax, hydrogenated oil or mixtures thereof.

9. The abuse-deterrent oral dosage form according to claim 1 or 2, wherein the oral dosage form is a capsule or a tablet.

10. The abuse-deterrent oral dosage form according to claim 1 or 2, wherein the oral dosage form further comprises an antioxidant.

11. The abuse-deterrent oral dosage form of claim 10, wherein the antioxidant comprises butylated hydroxy toluene (BHT); ascorbic acid, its salts and esters; Vitamin E, tocopherol and its salts; sodium metabisulphite; cysteine; citric acid; propyl gallate; butylated hydroxyanisole (BHA); or combinations thereof.

12. The abuse-deterrent oral dosage form according to claim 1 or 2, wherein each microparticle further comprises an enteric coat.

13. The abuse-deterrent oral dosage form according to claim 1 or 2, wherein the oral dosage form is a controlled-release oral dosage form.

14. The abuse-deterrent oral dosage form according to claim 1 or 2, wherein each microparticle further comprises a pharmaceutically acceptable surfactant.

15. The abuse-deterrent oral dosage form according to claim 1 or 2, wherein the microparticles are spherical.

16. The abuse-deterrent oral dosage form according to claim 1 or 2, wherein the one or more drugs prone to abuse is a stimulant.

17. The abuse-deterrent oral dosage form of claim 16, wherein the stimulant is amphetamine, methamphetamine or methylphenidate.

18. The abuse-deterrent oral dosage form according to claim 2, wherein the one or more drugs prone to abuse is uniformly dispersed in the carrier material of each microparticle.

19. The abuse-deterrent oral dosage form according to claim 2, wherein each microparticle comprises one or more fatty acids as carrier materials in an amount sufficient to solubilize the one or more drugs prone to abuse in the carrier material(s).

* * * * *

UNITED STATES PATENT AND TRADEMARK OFFICE
CERTIFICATE OF CORRECTION

PATENT NO. : 8,557,291 B2  
APPLICATION NO. : 12/473073  
DATED : October 15, 2013  
INVENTOR(S) : Roman V. Rariy et al.

Page 1 of 1

It is certified that error appears in the above-identified patent and that said Letters Patent is hereby corrected as shown below:

In the Claims

Claim 15, column 20, line 19 (claim 15, line 2):

change "microparticl es" to --microparticles--

Signed and Sealed this
Fourteenth Day of October, 2014

Michelle K. Lee
*Deputy Director of the United States Patent and Trademark Office*